US010796431B2

(12) United States Patent
Iglehart et al.

(10) Patent No.: US 10,796,431 B2
(45) Date of Patent: Oct. 6, 2020

(54) TARGETED DEPOSITION OF DENTAL CARE COMPOUNDS

(71) Applicant: TCMS Transparent Beauty, LLC, Austin, TX (US)

(72) Inventors: David C. Iglehart, Wimberley, TX (US); Albert D. Edgar, Austin, TX (US)

(73) Assignee: TCMS Transparent Beauty, LLC, Austin, TX (US)

(*) Notice: Subject to any disclaimer, the term of this patent is extended or adjusted under 35 U.S.C. 154(b) by 101 days.

(21) Appl. No.: 16/093,232

(22) PCT Filed: Apr. 12, 2017

(86) PCT No.: PCT/US2017/027094
§ 371 (c)(1),
(2) Date: Oct. 12, 2018

(87) PCT Pub. No.: WO2017/180681
PCT Pub. Date: Oct. 19, 2017

(65) Prior Publication Data
US 2019/0080451 A1 Mar. 14, 2019

Related U.S. Application Data

(60) Provisional application No. 62/321,436, filed on Apr. 12, 2016.

(51) Int. Cl.
G06K 9/00 (2006.01)
G06T 7/00 (2017.01)
(Continued)

(52) U.S. Cl.
CPC .......... *G06T 7/0012* (2013.01); *A61B 5/4547* (2013.01); *A61C 19/04* (2013.01);
(Continued)

(58) Field of Classification Search
CPC ..... A61B 5/4547; A61C 19/04; A61C 19/063; A61C 19/066; G01J 2003/102;
(Continued)

(56) References Cited

U.S. PATENT DOCUMENTS

2004/0252303 A1  12/2004  Giorgianni
2007/0035815 A1   2/2007  Edgar et al.
(Continued)

FOREIGN PATENT DOCUMENTS

CN   101641161   2/2010
CN   106488729   3/2017

OTHER PUBLICATIONS

Authorized officer Shane Thomas, International Search Report/ Written Opinion in PCT/US2017/027094 dated Jun. 28, 2017, 13 pages.

(Continued)

*Primary Examiner* — Charles T Shedrick
(74) *Attorney, Agent, or Firm* — Fish & Richardson P.C.

(57) ABSTRACT

Methods, systems, and apparatus, including computer programs encoded on a computer storage medium, for receiving an image of the area of the mouth. Identifying a feature of interest within the image. Determining an actual reflectance and an actual topology of the feature of interest. Determining a desired reflectance and a desired topology of the feature of interest. Calculating an amount of DCA to be applied to a portion of the feature of interest based on comparing the actual reflectance to the desired reflectance and the actual topology to the desired topology. Causing the calculated amount of DCA to be applied to the portion of the feature of interest.

20 Claims, 6 Drawing Sheets

(51) Int. Cl.
    *A61C 19/04*   (2006.01)
    *A61C 19/06*   (2006.01)
    *G01J 3/02*    (2006.01)
    *G01J 3/10*    (2006.01)
    *G01J 3/50*    (2006.01)
    *G06K 9/32*    (2006.01)
    *G06K 9/46*    (2006.01)
    *G06T 7/73*    (2017.01)
    *A61B 5/00*    (2006.01)
    *G01J 3/28*    (2006.01)

(52) U.S. Cl.
    CPC .......... *A61C 19/063* (2013.01); *A61C 19/066* (2013.01); *G01J 3/027* (2013.01); *G01J 3/0224* (2013.01); *G01J 3/10* (2013.01); *G01J 3/108* (2013.01); *G01J 3/508* (2013.01); *G06K 9/3233* (2013.01); *G06K 9/46* (2013.01); *G06T 7/73* (2017.01); *G01J 2003/102* (2013.01); *G01J 2003/2813* (2013.01); *G06T 2207/30036* (2013.01)

(58) Field of Classification Search
    CPC .. G01J 2003/2813; G01J 3/0224; G01J 3/027; G01J 3/10; G01J 3/108; G01J 3/508; G06K 9/3233; G06K 9/46; G06T 2207/30036; G06T 7/0012; G06T 7/73
    USPC ........................................................ 382/128
    See application file for complete search history.

(56) References Cited

U.S. PATENT DOCUMENTS

| | | |
|---|---|---|
| 2007/0049832 A1 | 3/2007 | Edgar et al. |
| 2008/0192999 A1 | 8/2008 | Edgar et al. |
| 2008/0193195 A1 | 8/2008 | Edgar et al. |
| 2008/0194971 A1 | 8/2008 | Edgar et al. |
| 2008/0219528 A1 | 9/2008 | Edgar et al. |
| 2009/0025747 A1 | 1/2009 | Edgar et al. |
| 2012/0155908 A1* | 6/2012 | Ito .................... G03G 15/5029 399/81 |
| 2013/0302078 A1 | 11/2013 | Edgar et al. |
| 2014/0200865 A1 | 7/2014 | Lehmann |
| 2015/0196109 A1 | 7/2015 | Edgar |

OTHER PUBLICATIONS

International Preliminary Report on Patentability for International Application No. PCT/US2017/027094, dated Oct. 25, 2018, 6 pages.
EP Extended European Search Report in European Application No. 1778309.7, dated Mar. 28, 2019, 7 pages.
CN Office Action in Chinese Appln. No. 201780031572.8, dated Aug. 13, 2020, 10 pages (with English Translation).

* cited by examiner

TARGETED DEPOSITION OF DENTAL CARE COMPOUNDS

CROSS-REFERENCE TO RELATED APPLICATION

This patent application claims the benefit of the filing date of U.S. Provisional Patent Application 62/321,436, filed Apr. 12, 2016, entitled "TARGETED DEPOSITION OF DENTAL CARE COMPOUNDS", the subject matter of which is incorporated herein by reference in its entirety.

This application is a national phase application under 35 U.S.C. § 371 of PCT International Application No. PCT/US2017/027094, filed on Apr. 12, 2017, which claims the benefit of U.S. Provisional Patent Application Ser. No. 62/321,436, filed on Apr. 12, 2016. The entire contents of the foregoing applications are hereby incorporated by reference.

BACKGROUND

Areas of the mouth, such as the surfaces of teeth, often become unattractive because of discolorations associated with stains, disease, deposits, cracks, age or other problems. For example, stains on teeth may be caused by foods like coffee or by fluorosis through excessive exposure to fluorides. Manual application of dental agents (e.g., whitening agents) can be imprecise, which may make manually-applied dental agents less effective. For example, some whitening agents can be harmful to soft tissue, such as gums; therefore, such agents must be applied by a professional or in a diluted form.

SUMMARY

Implementations of the present disclosure include methods for selectively applying a dental care agent (DCA) to an area of the mouth.

In general, innovative aspects of the subject matter described in this specification can be embodied in methods that include the actions of receiving an image of the area of the mouth. Identifying a feature of interest within the image. Determining an actual reflectance and an actual topology of the feature of interest. Determining a desired reflectance and a desired topology of the feature of interest. Calculating an amount of DCA to be applied to a portion of the feature of interest based on comparing the actual reflectance to the desired reflectance and the actual topology to the desired topology. Causing the calculated amount of DCA to be applied to the portion of the feature of interest. Other implementations of this aspect include corresponding systems, apparatus, and computer programs, configured to perform the actions of the methods, encoded on computer storage devices. These and other implementations can each optionally include one or more of the following features.

In some implementations, the feature of interest is a tooth. In some implementations, the feature of interest is a soft tissue. In some implementations, determining the desired reflectance and the desired topology of the feature of interest include removing areas of high spatial frequency from the actual reflectance and actual topology of the feature of interest.

In some implementations, the feature of interest is a tooth and the method includes determining an actual orientation of the tooth. Determining a desired orientation of the feature of tooth. Determining a second amount of DCA and a second portion of the tooth on which to apply the second amount of DCA to give the tooth an appearance of having the desired orientation. Causing the second amount of DCA to be applied to the second portion of the tooth.

In some implementations, the feature of interest is a first tooth and the method includes identifying a second tooth within the image. Determining an actual position of the first tooth relative to the second tooth. Determining a desired position of the first tooth relative to the second tooth. Determining a second amount of DCA and a second portion of the first tooth on which to apply the second amount of DCA to give the first tooth an appearance of having the desired position relative to the second tooth. Causing the second amount of DCA to be applied to the second portion of the first tooth.

In some implementations, the feature of interest is a tooth and the method includes identifying an interface between the tooth and a soft tissue within the image and causing a barrier DCA to be applied to the interface between the tooth and the soft tissue. In some implementations, the interface between the tooth and a soft tissue is identified based on colors within the image.

In some implementations, the method includes determining an average direction of light that impinges a surface of the feature of interest, and the desired reflectance and desired topology of the feature of interest are determined based on the average direction of light.

In some implementations, the method includes sending the image to a dental monitoring system. In some implementations, the method includes identifying a dental condition of the feature of interest, and sending an indication of the dental condition to a dental monitoring system.

The present disclosure further provides handheld devices for implementing the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1:
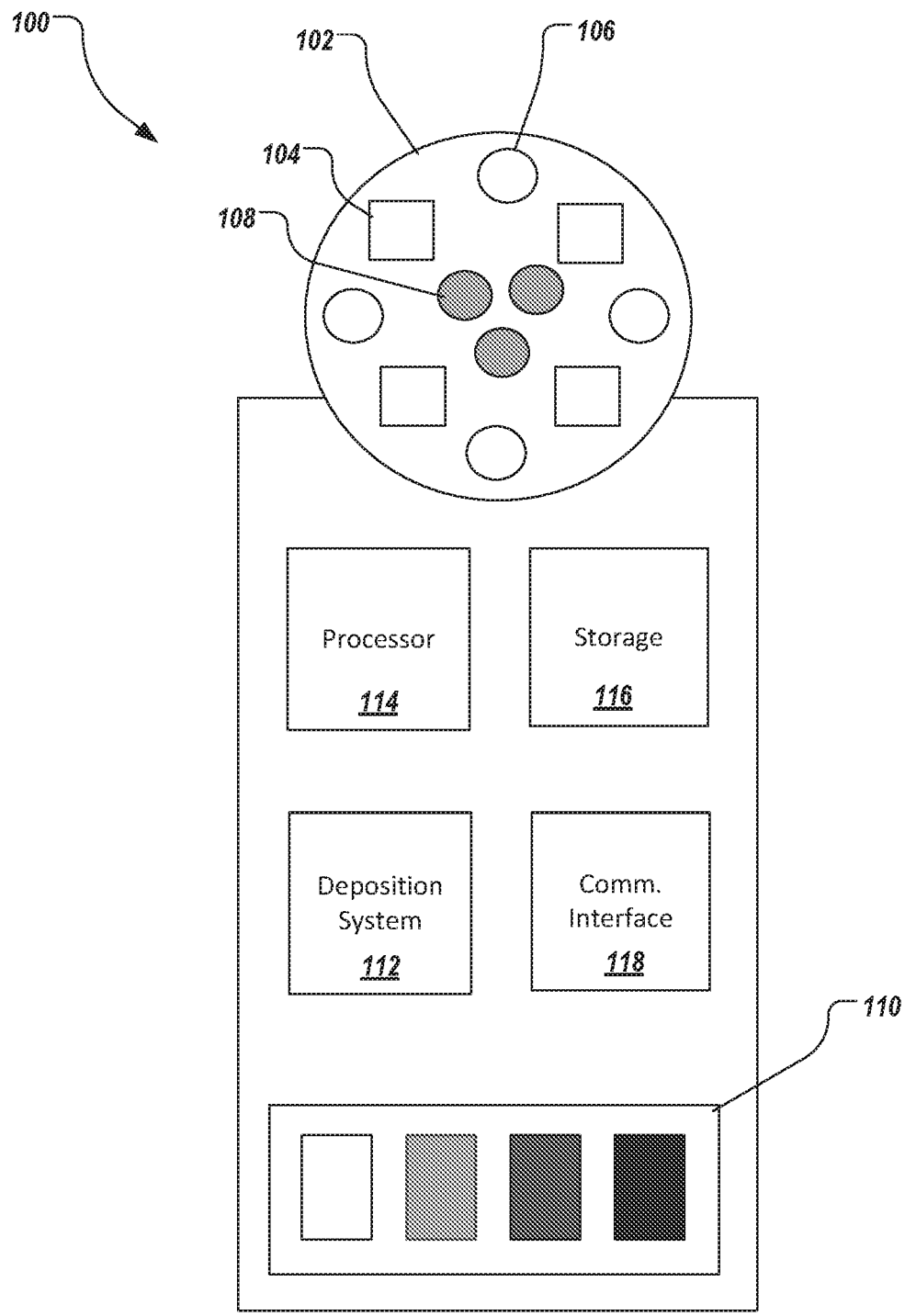
FIG. 1 depicts a block diagram of an example applicator device.

Implementations of the present disclosure generally build on apparatus and methods disclosed in each of U.S. patent application Ser. No. 11/503,806 (US20070035815), entitled "System and Method for Applying a Reflectance Modifying Agent to Improve the Visual Attractiveness of Human Skin," and filed on Aug. 14, 2006; U.S. patent application Ser. No. 11/503,629 (US20070049832), entitled "System and Method for Medical Monitoring and Treatment Through Cosmetic Monitoring and Treatment," and filed on Aug. 14, 2006; U.S. patent application Ser. No. 12/029,524 (US20080194971), entitled "System and Method for Applying a Reflectance Modifying Agent Electrostatically to Improve the Visual Attractiveness of Human Skin," and filed on Feb. 12, 2008; U.S. patent application Ser. No. 12/028,836 (US20080219528), entitled "System and Method for Providing Simulated Images through Cosmetic Monitoring," and filed on Feb. 11, 2008; U.S. patent application Ser. No. 12/028,835 (US20080193195), entitled "Handheld Apparatus and Method for the Automated Application of Cosmetics and Other Substances," and filed on May Feb. 11, 2008; U.S. patent application Ser. No. 12/029,534 (US20080192999), entitled "System and Method for Applying a Reflectance Modifying Agent to Change a Person's Appearance Based on a Digital Image," and filed on Feb. 12, 2008; U.S. patent application Ser. No. 12/129,624 (US20090025747), entitled "Apparatus and Method for the Precision Application of Cosmetics," and filed May 29, 2008; and U.S. patent application Ser. No. 13/946,170 (US2013010207), entitled "Apparatus and Method for Rapid and Precise Application of Cosmetics," and filed Jul. 19, 2013, The disclosures of the above-identified patent applications are expressly incorporated herein by reference in their entireties.

In the present disclosure, the term dental care agent (DCA) refers to any appropriate compound and/or form of energy useful for altering the reflectance of, or improving the health of, an area of the mouth, for example, the surfaces of teeth and/or gums. Examples of DCAs can include inks, dyes, pigments, bleaching agents, surfactant agents, chemically altering agents, steam, water and other appropriate substances that can alter the reflectance of teeth and other features and bioactive compounds and medicines that can improve health. A DCA composition is a composition that includes at least one DCA. A DCA composition can include other ingredients such as a carrier, binding agents, or an active ingredient such as a beneficial compound. A transparent DCA can be provided as a dye or a dilute pigment. An opaque DCA can include high refractive index particles. In some examples, the DCA can include pigments and a binder agent that adhere temporarily to areas of the mouth (e.g., teeth and gums). For example, such DCAs can be brushed off at night and reapplied the next morning.

The term frexel is defined as a small pixel-like region of an area of a mouth, which may represent a single large pixel or a small number of pixels. More specifically, a pixel refers to the area of the deposition on a surface immediately below the deposition aperture of a cosmetic applicator, for example, an electrostatic airbrush applicator. For some embodiments, a pixel may represent an area of $1/15"$ to $1/5"$.

The term attribute means the local reflectance of an area of the mouth (e.g., a tooth or gum surface), the surface morphology of the area of the mouth, or both. The term attribute is a subset of the broader term characteristic, which refers to any measurable property of an area of the mouth. The terms "in register in agreement" or "in agreement" mean specifically applying a DCA in register to frexel attributes in a manner to accentuate one or more frexels of a feature such as applying a light DCA to lighten a light feature; applying a dark DCA to darken a dark feature; adding red DCA to a red frexel; and applying DCA to a raised area on a tooth to highlight the raised area. The terms "in register in opposition" or "in opposition" mean specifically applying a DCA in register to an area of the mouth in a manner to treat, conceal or cover one or more feature, such as applying a light DCA to a dark tooth feature to lighten the feature; applying a dark DCA to a light feature to darken the tooth surface; and applying a light DCA to a portion of a depression in a tooth to hide the depression.

The term "differentiated DCA" means a DCA that is deliberately selected to be darker (have less luminance) or lighter (have more luminance) than a desired color of an area of the mouth. The term "highly differentiated DCA" means a DCA that is deliberately selected to have substantially greater or less of the desired color of an area of the mouth. For example, this means that a nulling of a target defect can be achieved with a limited amount of DCA. The term "surface color" means the surface's hue, chroma, and luminance. For example, the hue, chroma, and luminance of the surface of a tooth. Perceived color is influenced by factors such as the actual color, lighting, and texture of a tooth.

The term "opacity" means the amount of coverage that the DCA provides over the substrate surface. There are two extremes. If a DCA is 100% opaque, a viewer would see the pure bulk color of the DCA. If a DCA is perfectly transparent, that is 0% opaque, a viewer would see the pure color of, for example, a tooth under the DCA. If a DCA is 50% opaque, a viewer would see a 50-50 average of the DCA and tooth color.

The term "sensor" refers to a photodiode, phototransistor, or other optical detector. In some embodiments, a camera functions as one or more sensor. A "sensor ring" refers to a housing for LEDs and other components such as sensors. The housing may be shapes other than annular.

A "DCA applicator" is a device which applies a DCA to an area of the mouth. For example, the DCA applicator may be a sprayer, including an electrostatic sprayer or airbrush sprayer, a drop control device, or other apparatus, including, in some implementations, an apparatus applying energy (e.g. light). A "deposition element" is a portion of a DCA applicator that applies a DCA, such as a sprayer, a drop control element, or both. A "scanning and DCA applicator" scans a portion of the surface of the teeth and uses scan data to control a deposition of one or more DCA. An example of a drop control element is an inkjet print head where individual droplets are precisely controlled. An example of a non-drop control element is a sprayer. Spray devices are non-drop control techniques where droplets are produced and controlled only in aggregate.

The terms "mean illumination" and "average direction of light" refer to the average angle and diffusion of light reaching a particular surface. This defines how surface irregularities are typically shaded by light, and therefore how the human visual system interprets form and texture. For example, in a "drop shadow" effect commonly used in the graphic arts industry to make text appear dimensional, as implemented in an exemplary fashion in Adobe Photoshop, the light is usually assumed to come from above the viewer, and the calculated shadows cast give an illusion of dimensionality to an image that is in reality flat. Inside the mouth, mean illumination usually comes through the front of the mouth opening, but also within that constraint, from above. The direction "above" may be determined by the orientation of facial features if they are visible, by the orientation of the device if the user is instructed to hold the device in a predetermined orientation, but, assuming the user is standing vertically (relative to gravity), the direction of "above" can also be oriented by sensing the direction of gravity using a sensor in the device.

The terms "reflectance," "optical density," or "density" refer to a measure of the reflection of an area of the mouth, such as a tooth surface. In this specification, an "initial reflectance" reading is an initial reflectance reading from a sensor, before compensating for distance or tilt. An "adjusted reflectance" reading compensates the initial reflectance reading for distance and tilt of a surface from a sensor ring. Adjusted reflectance is a reflectance reading corrected for device height and tilt relative to the tooth surface. A "desired reflectance" is typically a desired level of correction for an area of tooth surface, such as threshold for lightening the tooth surface, darkening it, or both.

The term handheld includes devices that are self-contained in a housing that may be held in a hand as well as devices where a housing is tethered to power supply and/or computer.

Implementations of the present disclosure are generally directed to apparatus and methods for rapid and precise application of dental care agents (DCAs), including dyes and pigments, to an area of the mouth. Implementations of the present disclosure provide control of a handheld deposition device to rapidly apply relatively small amounts of a DCA in register with or in opposition to measured attributes. In some implementations, one or more sensors, such as one or more cameras, and an image processing system view an area of the mouth. A processor activates a deposition system to apply one or more DCAs to a location known to the processor relative to an image of the mouth.

As discussed in further detail herein, deposition devices in accordance with implementations of the present disclosure can include at least one deposition element that is controlled by a processor. The processor processes data obtained from one or more sensors that are responsive to light reflected from an area of the mouth (e.g., teeth and gums). Each of the one or more sensors can include a sensor that is sensitive to the amount of reflected light in one or more wavelengths. Example sensors can include, but are not limited to, one or more cameras, one or more photodiodes and/or one or more phototransistors. One or more illuminators, also termed light sources, can be provided. Each light source can include a light emitting diode (LED). In some implementations, the multiple light sources are turned on simultaneously in order to provide a uniform lighting. In this manner, reflectance can be accurately measured with sufficient illumination to permit the use of a polarizing filter. The use of multiple light sources provides additional flexibility to sequence the light sources to provide different lighting states. In this manner, data indicative of tooth and gum reflectance and topology can be obtained. The use of multiple light sources also enables a pairing of one or more light sources with one or more photodiodes, for example. In some implementations, a single light source, such as a ring light, can be provided.

Implementations of the present disclosure include using motion for scanning and deposition. In particular, a user of the handheld deposition device moves the deposition device manually across an area of the mouth. The movement can correspond to the familiar and instinctive pattern of moving a toothbrush. As the handheld deposition device is caused to move over the area of the mouth, the deposition device scans a plurality of frexels. The deposition device automatically deposits one or more DCAs in response to the reflectance attributes of the frexels to improve the appearance of the area of the mouth. Movement of the deposition device can include any pattern or combination of patterns.

Implementations of the present disclosure include the use of multiple deposition nozzles. In particular, the use of multiple deposition nozzles can increase the speed and effectiveness of sensing, analysis and deposition. For most users, the handheld deposition device is most freely usable if it is directionally agnostic, that is, if it can be moved in any direction. The use of multiple deposition nozzles enables the deposition device to be directionally agnostic. In some implementations, the multiple deposition nozzles can be arranged in a non-linear pattern. For example, multiple deposition nozzles arranged in a linear pattern provides two "ideal" directions of motion (e.g., forward and backward along a linear axis running through the two deposition nozzles). A triangle arrangement of three deposition nozzles within a generally circular pattern provides six "ideal" directions of motion as opposed to two "ideal" directions of motion for three heads arranged in a line. With a large number of deposition nozzles, arrangement in a pure circle may provide excessive overlap of head trajectories on the edge of the circle parallel to the direction of motion. A uniform density across an area, such as the area enclosed by a circle, can provide a more uniform coverage in all directions as the handheld device is moved.

Figure 2:
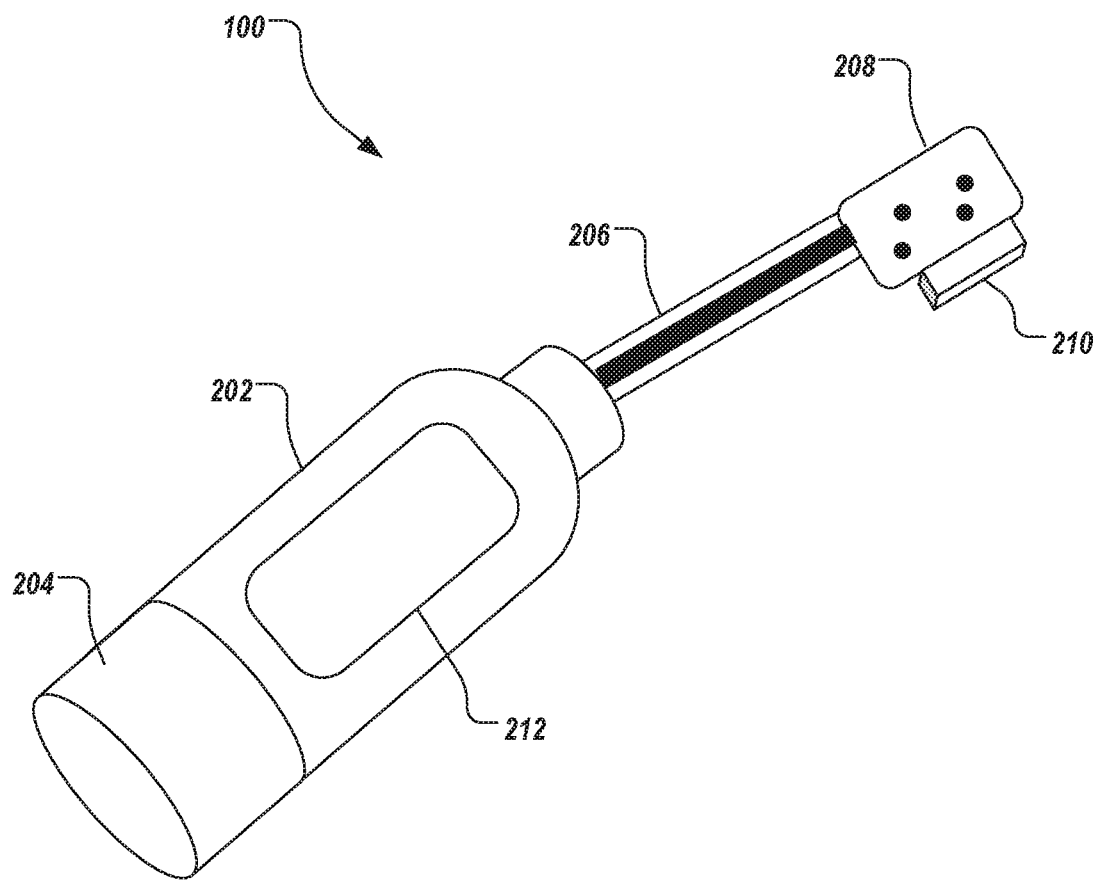
FIG. 2 depicts a perspective view of an example applicator device.
Figure 3:
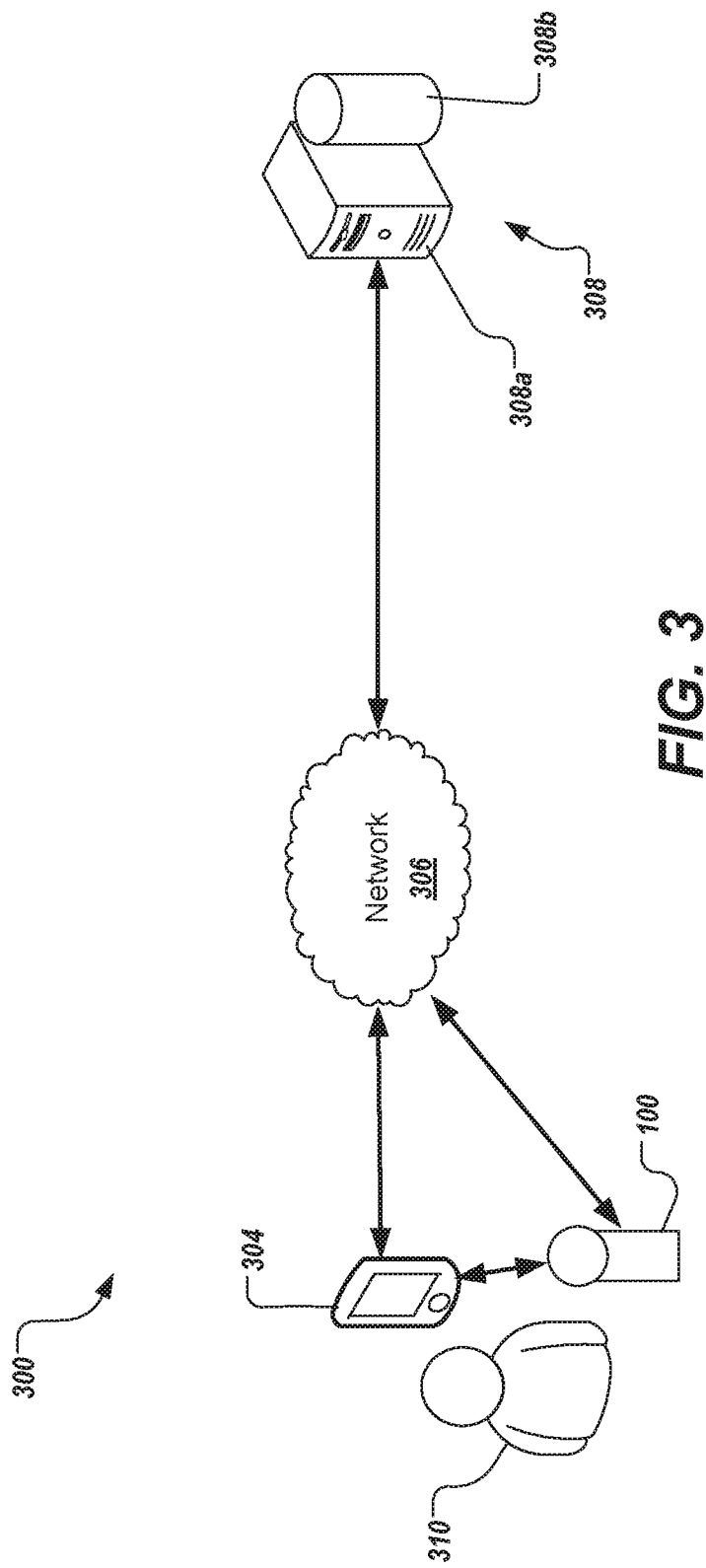
FIG. 3 depicts an example communication system including an example applicator device.

Referring now to FIGS. 1-3 an example handheld applicator device 100 will be discussed in detail. FIG. 1 depicts a block diagram of an example applicator device 100. The applicator device 100 includes an imaging head 102. The imaging head 102 provides a source of illumination that can provide uniform distribution of light. The imaging head 102 further enables an adequate intensity of the distributed light for sensing the area of the mouth to be treated.

The imaging head 102 includes one or more illuminators 104 and at least one sensor 106. In some implementations, the illuminators 104 are provided as one or more LEDs. In some implementations, the illuminators 104 include LEDs positioned a short distance from a filter (e.g., a circular polarizing filter), discussed in further detail below, on the same side as a sensor, also discussed in further detail below. In this manner, the illuminators provide ample light for reflectance measurement. In some implementations, a high brightness of the LEDs permits the applicator device 100 to be effective in ambient lighting conditions. In addition, the imaging head 102 includes at least one sensor 106, for example, a camera to obtain images of the mouth.

In some examples, the illuminators 104 can be located in the front and back and around the sides of the imaging head 102, for example, to allow for the creation of soft lighting (e.g., diffused and reflected light). Such soft lighting may help reduce random texture readings during imaging of a user's mouth that are caused, for example, by movements of the imaging head 102 of the applicator device 100 and the interference of shadows. Soft lighting may further reduce specular reflection, for example, by allowing the integration of sensed data collected from many angles around an area of the mouth.

In some examples, the illuminators 104 emit red light. In some examples the illuminators emit other colors, for example, yellow and orange. In some examples, multiple colors concurrently, for example red-green-blue (RGB) colors.

In some implementations, the illuminators 104 can be visible light sources (e.g., LEDs) under a circular polarizing filter. For example, the circular polarizing filter may aid in reducing glare from teeth. In some implementations, one or more of the illuminators 104 can be infrared light sources and the sensors 106 can include corresponding infrared sensors. In some implementations, one or more of the illuminators 104 can be ultraviolet light sources and the sensors 106 can include corresponding ultraviolet sensors.

The applicator device 100 further includes a nozzle 108. The nozzle 108 is a deposition element that provides an outlet of the deposition system, and is used to jet one or more DCAs onto the surface to be treated. For example, DCAs can include, but are not limited to, teeth whitening agents, dyes, pigments, bleaching agents, gum treatment agents, barrier agents, for example iron oxide or Phillips Liquidam® products) and therapeutic agents. In some implementations, multiple nozzles 108 may be used to increase the speed of deposition. For example, three nozzles 108 can be provided. Each nozzle 108 can correspond to the same DCA (e.g., type and/or color), or can correspond to different DCAs type and/or color). In some implementations, each nozzle 108 can be activated to deposit a DCA when a target area is directly underneath the particular nozzle 108, and can be activated independently of the other nozzles 108.

One or more removable reservoirs 110 are provided. Each removable reservoir 110 can be provided as a cartridge that contains a DCA. In some implementations, a single reservoir 110 is provided, such that the applicator device 100 deposits a single DCA (e.g., type and/or color). In some implementations, multiple reservoirs 110 are provided, such that the applicator device 100 deposits one or more different DCAs (e.g., type and/or color). The reservoir 110 is in fluid communication with the nozzle 108 through a deposition system 112. The deposition system 112 can include fluid channels (e.g., conduits), valves, and a pressure source (not shown). The deposition system 112 can be used to control the transfer of DCA from the reservoir 110 to the nozzles 108 for application to an area of the mouth.

The applicator device 100 further includes a processor 114 for executing instructions stored in electronic storage 116. The processor 114 controls the illuminators 104, sensor 106, and deposition system 112 to obtain images of areas of the mouth and control deposition of DCA on the teeth or gums. In addition, the processor 114 executes instructions to perform operations as described in more detail below.

In some implementations, the applicator device 100 can also include a communications interface 118 to communicate with a user computing device or computing system as described in more detail below in reference to FIG. 3. The communications interface 118 can be a wired or wireless interface. For example, the communications interface 118 can be a USB, WiFi, Bluetooth, or a mobile telecommunications (e.g., 4G, LTE) interface. In some implementations, a mobile communication device may be integrated with the applicator device 100. For example, the applicator device 100 can include a display and an input interface a keypad or touch screen).

FIG. 2 depicts a perspective view of an example applicator device 100. The applicator device 100 includes a housing 202, a neck 206, and a sensor head 208. The housing 202 encloses and protects other components discussed herein. The housing 202 can be manufactured out of plastics and/or other materials, and can be shaped or contoured to ergonomically accommodate a human hand grasping the applicator device 100. The housing 202 can be configured to receive a cartridge 204 containing one or more types of DCA (e.g., reservoirs 110). The neck 206 is connected to the housing 202 of the applicator device 100. The neck 206 connects the housing and the sensor head 208. The neck 206 is configured to allow the sensor head 208 to reach into the back of a user's mouth (e.g., similar to a toothbrush). The sensor head 208 houses the imaging head 102 described above. In some examples, the sensor head 208 includes a guard 210 extending from the sensor head 208. The guard 210 is configured to maintain a proper distance between the illuminators 104 and sensors 106 of the imaging head 102 and areas of a user's mouth (e.g., the teeth and gums). In some implementations, the applicator device 100 includes a display 212 (e.g., an LCD display, a touchscreen display, etc).

Implementations of the present disclosure are further directed to methods for processing images, determining attributes, calculating enhancements, and activating deposition component. As discussed in further detail herein, methods of the present disclosure can be realized using digital electronic circuitry, or in computer hardware, firmware, software, or combinations thereof.

For example, as discussed in more detail below in reference to FIGS. 4-6, the applicator device 100 can scan attributes of an area of a mouth (e.g., teeth and gums). The applicator device 100 can obtain images of the user's mouth and identify characteristics of the teeth and gums. For example, a characteristic can include, but is not limited to, the reflectance of an area of a tooth or gum, the surface topology of a tooth (e.g., a chip), the orientation of a tooth, the position of a tooth relative to other teeth, etc. For example, spots, stains or discolored bands on teeth, such as those caused by hypocalcification white or dark spots, well-water stains, antibiotics, such as tetracycline, and even childhood illnesses while the teeth are developing can be identified in the images.

The applicator device 100 can process the images to determine a desired appearance for an identified characteristic. For example, the applicator device 100 can process the images to develop visual patterns on the teeth that can be used to increase the aesthetic attractiveness of teeth. Visual uniformity, morphology such as smoothness and roundness, translucence, opalescence and a sense of transparent depth are at least as important as degree of whiteness as a metric for aesthetic beauty in teeth. The applicator device 100 can process the images to develop such effects. For example, such spots, such as those described above, can be identified as local areas with of high spatial frequency variation in reflectance of a tooth. A filtering process can be applied to smooth the appearance of such areas and provide a more visually uniform look. The applicator device 100 can apply appropriate DCA to appropriate areas of the teeth or gums of a user to produce the desired appearance.

In some implementations scanned attributes of an area of a tooth, gums, or other feature are identified, and the automatic and precise deposition of one or more DCAs can be initiated on the area. In some implementations, the applicator device 100, is moved manually back and forth across the area in multiple passes (e.g., similar to the motion of brushing one's teeth). The applicator device 100 can continually scan and determine values of one or more attributes of the area relative to one or more threshold values. Example attributes can include lightness and darkness of the area of teeth or gums. The one or more threshold values can be set by means of the software and can correspond to a cosmetic improvement in the appearance of the area. In some implementations, the applicator device automatically deposits the one or more DCAs until the measured attribute values achieve the threshold value. For example, the applicator device can automatically deposit the one or more DCAs until the measured attribute values exceed or fall below the threshold value. In some implementations, the threshold value can correspond to a target value, where the applicator device automatically deposits the one or more DCAs until a difference between a measured attribute value and the threshold value falls below a threshold difference.

In some implementations, the movement of the applicator device may be random in the sense that the processor may not have control over the location of the point of deposition. For example, a user may move the applicator device over the area of the mouth in random patterns.

The processor may be programmed to know at any time the location of an aim point of potential deposition if the processor gave the command to fire. In this case, the aim point is said to be "nominated" by the, in some ways, random motion of the hand. The processor has the choice of "electing" the nominated point by "firing," or otherwise applying the cosmetic at that point, or may choose to wait for the next nominated point based on the movement of the hand, over which the processor is aware but does not have direct control. This is referred to as the "random nomination" approach, as distinguished from a system in which the processor has the ability to aim a deposition directly at a defect that it chooses.

In some implementations, an applicator device 100 can be configured to communicate with a user computing device or a remote computing system. FIG. 3 depicts an example system 300 in which an applicator device 100 is in communication with a user computing device 304 and a computing system 308, over one or more networks 306. Network 306 can include a large network or combination of networks, such as a local area network (LAN), wide area network (WAN), the Internet, a cellular network, a satellite network, one or more wireless access points, or a combination thereof connecting any number of mobile clients, fixed clients, and servers.

In some implementations, the applicator device 100 can be an electronic cosmetic applicator that applies DCA, such as cosmetics, to areas in the mouth of a user 310. The applicator device 100 can include one or more communication interfaces for sending and receiving data. The applicator device 100 may communicate with user computing device 304 through a wired communication channel (e.g., a universal serial bus (USB) connection) or a wireless communication channel such as a WAN (e.g., WiFi) or a personal area network (PAN) (e.g., Bluetooth). The applicator device 100 may communicate with computing system 308 through a network communication interface over network 306. For example, the applicator device 100 can communicate data or images of a user's 310 teeth and gums to the user computing device 304 for display to the user 310.

The computing system 308 can include a computing device 308a and computer-readable memory provided as a persistent storage device 308b, and can represent various forms of server systems including, but not limited to a web server, an application server, a proxy server, a network server, or a server farm. Furthermore, the computing device 308a can include one or more processors for executing instructions stored in storage device 308b and/or received from one or more other electronic devices, for example over network 306. In addition, these computing devices 308a also typically can include network interfaces and communication devices for sending and receiving data. For example, the computing system 308 can be a dental health monitoring system. The computing system 308 can received dental data such as images of the users 310 mouth (e.g., teeth and gums) from the applicator device 100.

The user computing device 304 can be any of a number of different types of computing devices including, for example, mobile phones; smartphones; personal digital assistants; laptop, tablet, and netbook computers; and desktop computers including personal computers, special purpose computers, general purpose computers, and/or combinations of special purpose and general purpose computers. The user computing devices 304 typically can have internal or external storage components for storing data and programs such as an operating system and one or more application programs. In particular, the internal or external storage components for user computing devices 304 can store a client application for interfacing with the applicator device 100.

The user computing devices 304 also typically include a central processing unit (CPU) for executing instructions stored in storage and/or received from one or more other electronic devices, for example over network 306. The user computing devices 304 also include one or more communication interfaces for sending and receiving data. One example of such communications interfaces is a modem. Other examples include antennas, transceivers, communications cards, and other network adapters capable of transmitting and receiving data over a network (e.g., network 306) through a wired or wireless data pathway.

In some implementations, the applicator device 100 can be in communication with a dental health monitoring system hosted by computing system 308. For example, the applicator device 100 can be configured to communicate directly with the computing system 308 through a network 306 or the applicator device 100 can communicate with the computing system 308 through the user computing device 304. The applicator device 100 can store images of a user's 310 mouth and send the images to the dental health monitoring system for analysis. For example, the images can be analyzed to identify dental health problems such as plaque, tartar, gingivitis, caries, and mouth cancers.

In some implementations, the applicator device 100 can be configured to perform specific imaging techniques for use in dental health analysis of a user's 310 mouth. For example, the applicator device 100 can include appropriate light sources and imaging sensors to perform techniques including, but not limited to, direct and induced ultraviolet fluorescence imaging, infrared penetration imaging, fluoroscopy, spectral fluorescence imaging, laser reflection imaging, transillumination imaging, and laser photothermal and luminescence imaging.

In some implementations, the applicator device 100 can perform the above described oral health analyses. In some examples, the applicator device 100 sends the analysis results to the dental health monitoring system. In some implementations, the dental health monitoring system can send data related to treatment products for presentation to a user on the user's computing device 304 or on a display of the applicator device 100.

In some examples, the applicator device 100 can be used to apply dental health treatments or therapeutic products to a user's 310 teeth and gums. For example, a DCA cartridge containing treatment agents such as fluorides, restorative or sealant products (e.g., bioactives and glass ionomers or other therapeutic products can be attached to an applicator device 100. The applicator device 100 can target the deposition of such DCAs on appropriate areas of a user's 310 teeth and gums. For example, such DCAs can used for the prevention or treatment of plaque, tartar, and gingivitis by targeting deposition of products at the gum line in the space between teeth in daily applications.

Figure 4:
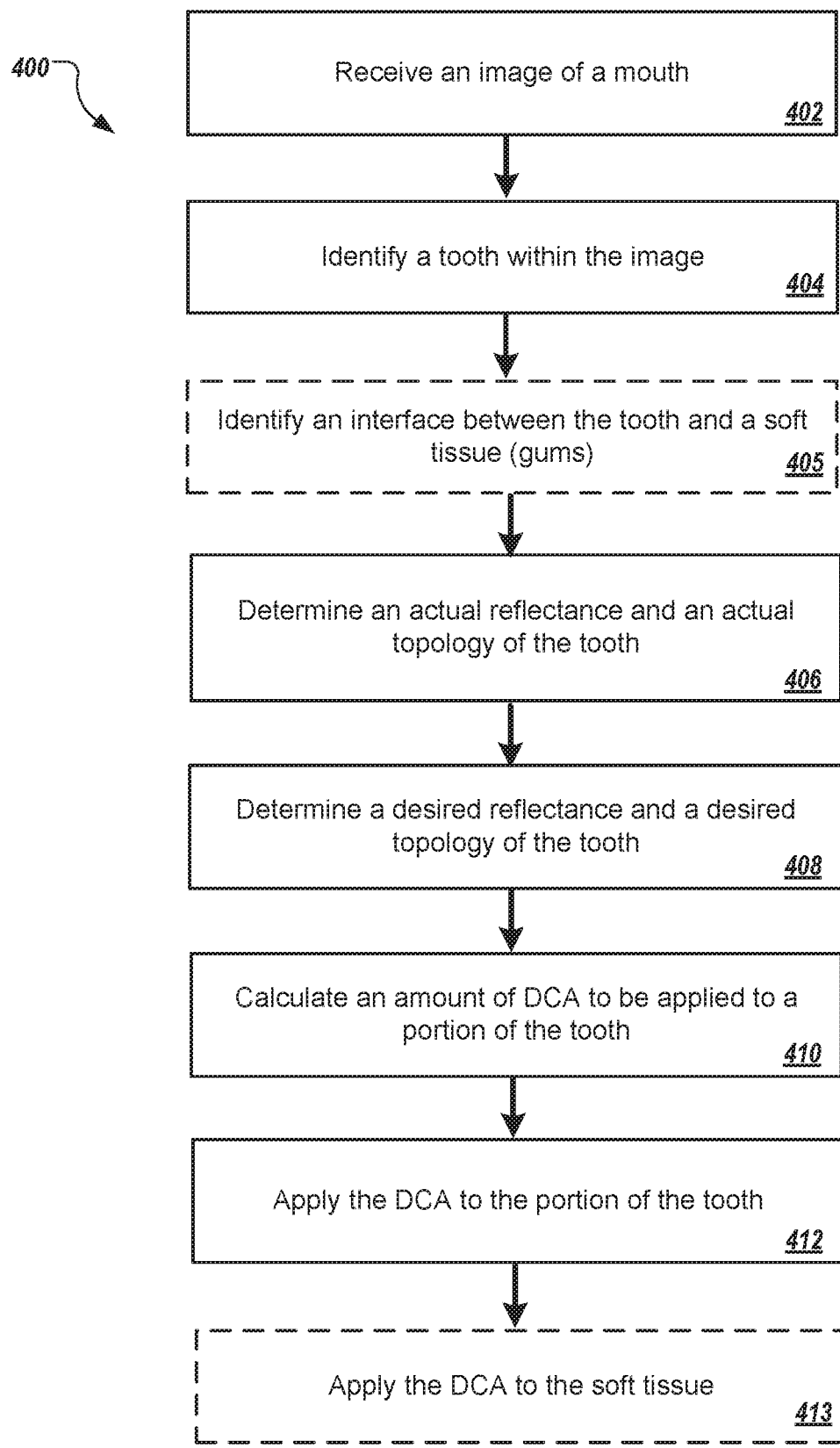
FIG. 4 depicts an example process for selectively applying a DCA to an area of a mouth.

FIG. 4 depicts an example process 400 for selectively applying a DCA to an area of a mouth that can be executed in accordance with implementations of the present disclosure. In some examples, the example process 400 can be provided as one or more computer-executable programs executed using one or more computing devices. In some examples, the process 400 is executed by an applicator device (e.g., applicator device 100 of FIGS. 1-3). In general, the example process includes operations 402-413. Operations 405 and 413 are illustrated using a dashed line to indicate that operations 405 and 413 are optional. In particular, operations 405 and 413 are directed to refinements of a general example process 400 and can be included in various implementations in accordance with the present disclosure.

An image of an area of a mouth is received (402). For example, the applicator device 100 of FIGS. 1-3 can be used to generate the image of the area of the mouth using a sensor 106 (e.g., a camera) and the illuminators 104. In some examples, the image can be filtered to remove noise. For example, the processor 114 of the applicator device 100 can apply a low-pass filter to the image to remove frequencies that are greater than a threshold frequency. In some examples, the applicator device 100 can generate multiple images of the area of the mouth using multiple sensors 106 (e.g., cameras). For example, each sensor 106 can obtain an image from a different direction.

A tooth is identified within the image (404). For example, image analysis techniques can be applied to the image to identify a tooth within the image. For instance, a tooth tends to be light in color near the middle and darker near the edges due, in part, to shadowing created by the curvature of the tooth. Image analysis techniques (e.g., edge detection techniques) can be applied to the image to identify the variations in color and detect the edges of the tooth. In some examples, regions of the tooth can be identified based on the shading and corresponding curvature of the tooth. For example, the sides, top edge, and bottom edge of the tooth can be identified.

An actual reflectance and an actual topology of the tooth are determined (406). For example, an actual reflectance and an actual topology of the tooth can be determined from the image. The actual reflectance can be for multiple regions or points on the tooth. For example, the actual reflectance can be calculated by averaging the tooth reflectance around the nominated point. The averaging can cover an area and weight approximately matching the area to be covered by and affected by a dot of DCA that would be deposited. The topology of the surface of the tooth can be determined based on the reflectance and shadows in the image. For example, the sensors 106 of the applicator device 100 can obtain images of the area of the mouth that includes the tooth from three or more different directions. In addition, the illuminators 104 can be controlled to illuminate the area of the mouth from directions corresponding to the sensor 106 that captures each image. The images can be processed to determine the topology of the tooth based on variations in the shadows in each image. In some examples, a three-dimensional model of the topology of the tooth can be generated based on the images.

A desired reflectance and a desired topology of the tooth are determined (408). For example, teeth are not opaque, but opalescent. Opaque teeth look artificial and unattractive. The illusion of opalescence and roundness can be amplified by varying the whiteness across the tooth. Moreover, slight variations in the reflectance (e.g., whiteness) of a tooth may be desirable as opposed to over a uniform whiteness across the tooth that comes from bleaching. For example, slight variations in the reflectance of a tooth may accentuate the tooth's natural topology (e.g., curvature) cover up undesired blemishes (e.g., chips). For example, the processor 114 of the applicator device 100 can determine a desired reflectance by applying different filters to various regions of the image. For example, a low-pass filter can be applied to the center of the tooth to remove spatial frequencies that are greater than second threshold frequency. For example, in the middle of the tooth it may be desirable to have minimal variation in the reflectance (e.g., a more uniform appearance may be desired). At the edges of the tooth (e.g., at points of the tooth's natural curvature), a low-pass filter using a different, third threshold frequency, a band-pass filter, or a gradient filter can be applied. For example, at the edges of the tooth it may be desirable to have variations in reflectance.

In some implementations, the techniques of the present invention for the identification and targeting of specific visual patterns on the teeth themselves can be used to increase the aesthetic attractiveness of teeth. For example, such techniques can be used to enhance the visual uniformity, morphology such as smoothness and roundness, translucence, and opalescence of teeth. For example, the desired reflectance and desired topology for the tooth can be determined by removing areas of high spatial frequency.

In some implementations, the desired reflectance and topology of the tooth can be determined based on user selected input. For example, a user can be permitted to select or upload data that indicates the user's desired appearance for her teeth. For example, the user may be permitted to select visual effects to be applied to the user's teeth. Visual effects can include, for example, temporary colors, images, or other "looks." In such implementations, the applicator device 100 can determine the desired reflectance and desired topology by mapping the selected visual effects to the reflectance and topology of the user's teeth.

In some implementations, an average direction of light that impinges the surface of the tooth is determined. The direction of light impinging on the surface of a tooth may affect the desired appearance of a tooth. For example, teeth are generally viewed from the front of the mouth. That is, teeth are not generally viewed from side angles. Thus, it can be advantageous to determine the average direction of light that impinges the tooth's surface. The direction of light can be determined, for example, based on shadows in the image. In some examples, the applicator device 100 can be configured to determining the location of the tooth within the mouth. The location of the tooth can be determined by identifying the type of the tooth (e.g., a central incisor tooth vs. a cuspid vs. a molar) based on its shape and position relative to other teeth. The location of the tooth can be used to determine the average direction of light that will impact the tooth. For example, if the tooth is on the side of the mouth (e.g., a molar) light will impact the tooth at a relatively narrow angle, whereas if the tooth is at the front of the mouth (e.g., a central tooth) light will impact the tooth at an angle normal to (or nearly normal to) the surface of the tooth. The desired reflectance and desired topology of the tooth can be modified based on the average direction of light that will impinge the tooth.

An amount of DCA to be applied to a portion of the tooth is calculated (410). For example, an amount of DCA to be applied to a portion of the tooth based on comparing the actual reflectance to the desired reflectance and the actual topology to the desired topology. For example, the applicator 100 can calculate an amount of DCA to be added to various portions of the tooth based on a calculated difference between the actual reflectance to the desired reflectance and the actual topology to the desired topology, and the reflectance or opacity of the DCA in order to achieve the desired appearance of the tooth.

Furthermore, the applicator 100 may not apply DCA to the entire surface of the tooth, but only to particular portions of the tooth. For example, two points on the front surface tooth may have respective reflectances of 50% and 70%. Applying a whitening DCA uniformly may result in respective reflectances of 70% and 82%; thus, an undesired variation still remains. However, by applying the DCA only to the darker portion, a more uniform reflectance can be achieved overall.

The DCA is applied to the portion of the tooth (412). For example, the processor 114 of the applicator device 100 can control the depositions system 112 to apply the appropriate amount of DCA to various portions of the tooth. In some implementations, the processor 114 can be made aware of motion of the handheld device (e.g., the applicator device 100) by means of processing the series of past and present images. In some implementations, the processor can monitor movement of the handheld device based on signals generated by an accelerometer. Using estimators based on momentum, a likely future path including the locus of future points of the tooth relative the current image can be calculated. The processor can review these predicted future points and pick a predicted portion of the tooth and predicted time to apply the DCA that corresponds to a maxima along the line of motion closer to the center of a defect. Functionally, this enables the processor 114 to "aim" by controlling time in the one dimension of movement of the hand.

In some implementations, the example process 400 can include the operation 405. In particular, an interface between the tooth and a soft tissue is identified (405). For example, soft tissue (e.g., gums, lips, tongue) can be distinguished from teeth by the ratio of reflected red light to green light. For example, the image layers (e.g., Red-Green-Blue color layers) can be processed and edges can be detected to identify the interface between the teeth and soft tissue. In some implementations, fluorescent light can be used to distinguish between teeth and soft tissues.

In some implementations, the example process 400 can include the operation 413. In particular, DCA is applied to the soft tissue (413). For example, one type or pigment of DCA can be applied to teeth and a different type or pigment of DCA can be applied to gums. For example, the color and patterns on gums can also be enhanced cosmetically through targeted deposition of DCAs. For example, a process similar to that described above for applying DCA to a tooth can be performed for soft tissue. The applicator 100 can determine the actual reflectance and a desired reflectance of the soft tissue from the image. The desired reflectance of the soft tissue can be determined based on processing the image to remove undesirable features and/or to darken the soft tissue. For example, a dark pigmented DCA may be applied to the gums to increase the contrast between teeth and gums. Consequently, the increased contrast between teeth and gums may cause the teeth to appear "whiter" without applying a whitening DCA to the teeth. The type and amount of DCA to be applied can then be calculated based on the actual and desired reflectances, and applied to the appropriate portions of the soft tissue.

In some examples, a barrier agent can be applied to the interface between the teeth and soft tissue. For example, barrier DCAs (e.g., iron oxide, Phillips Liquidam® products) can be applied precisely to the margin between the teeth and the gums to form a barrier between the two and limit the exposure of the gums to active DCAs. In some examples, the barrier agent can be applied as a preparatory step before applying an active DCA to the teeth which, if the active DCA were to contact the soft tissue, may be harmful to the soft tissue. For example, such techniques can be used to apply whitening agents (e.g., hydrogen peroxide based whitening polymers, whitening varnishes) only to the teeth, and may help reduce damage to the gums, such as chemical burning. Such techniques may allow stronger active DCAs to be used on the teeth without harming the soft tissue.

In some implementations, techniques can be applied to alter the appearance of a tooth's orientation or position relative to other teeth. In other words, techniques can be applied to give the appearance of altering the dimensionality of a tooth. For example, total uniformity in dimension gives teeth a flat, painted, plastic look. Teeth have dimension that is seen by shadowing. In some implementations, DCAs can be applied to enhance and/or create shadowing effects on teeth so as to change the dimensional appearance (e.g., orientation and position) of teeth.

Figure 5:
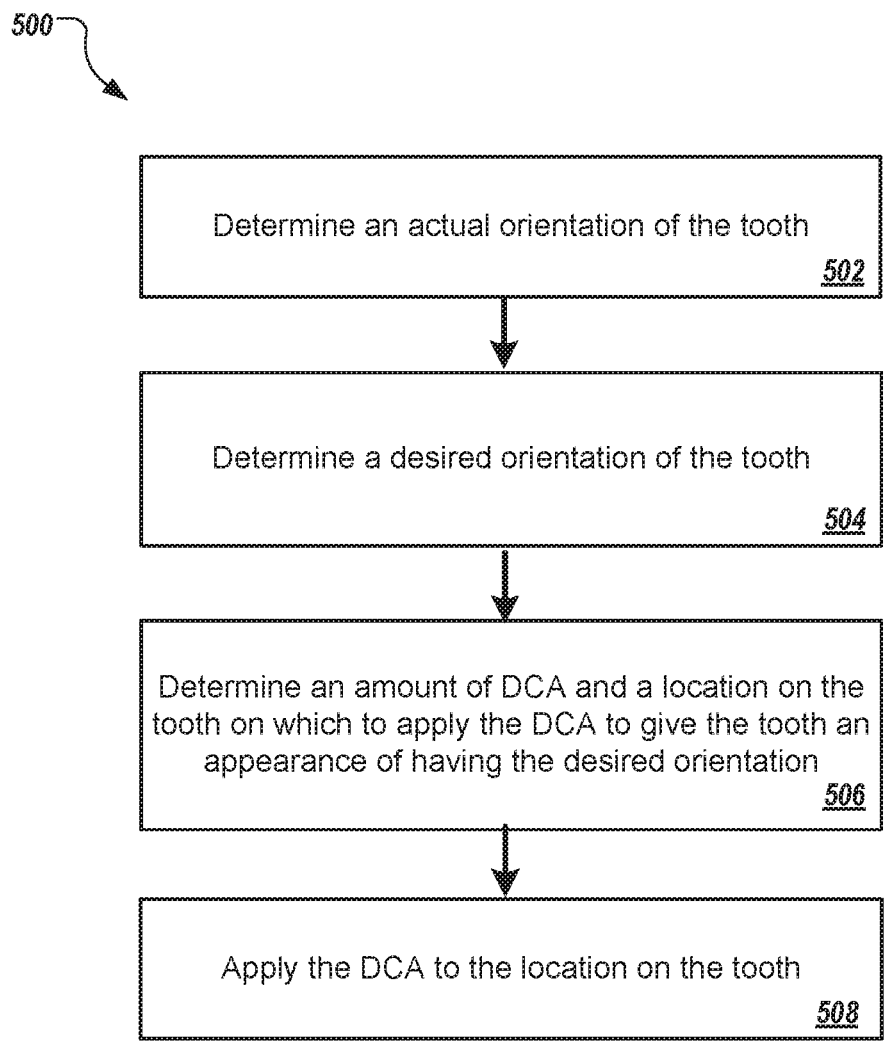
FIG. 5 depicts an example process for selectively applying a DCA to a tooth to adjust the apparent orientation of a tooth.

FIG. 5 depicts an example process 500 for selectively applying a DCA to a tooth to adjust the apparent orientation of a tooth that can be executed in accordance with implementations of the present disclosure. In some examples, the example process 500 can be provided as one or more computer-executable programs executed using one or more computing devices. In some examples, the process 500 is executed by an applicator device (e.g., applicator device 100 of FIGS. 1-3).

An actual orientation of a tooth is determined (502). For example, the orientation of the tooth can be determined based on detecting the edges of the tooth within the image, as described above. For example, the orientation can be determined based on the shadowing of the tooth, due to the tooth's curvature. In some examples, as discussed above, a three-dimensional model of the area of the mouth can be generated from images of the area of the mouth. The orientation of the tooth can be determined from the three-dimensional model. The orientation can include, for example, an angle of the tooth relative to the gums (e.g., the vertical angle of the tooth) to determine if a tooth is crooked and/or an angle of the tooth relative to the average direction of light on the tooth's surface to determine if the tooth is twisted. For example, a crooked tooth is a tooth which is canted relative to an axis extending normal to the jaw. A twisted tooth is a tooth in which an external surface of the tooth is twisted about the axis extending normal to the jaw (e.g., a front surface of a twisted tooth does not directly face the outside of the mouth). In some examples, the orientation of the tooth can be determined relative to other teeth. For example, a normal orientation can be determined based on all of the detected teeth within an image or multiple images. The orientation of a particular tooth can be compared to the expected orientation of the particular tooth and/or the actual orientations of neighboring teeth.

A desired orientation of the tooth is determined (504). For example, the desired orientation can be chosen to correspond to respective orientation of neighboring teeth such that the tooth does not appear crooked or twisted. In some examples, the desired orientation of the tooth can be determined based on a standard model of human teeth (e.g., a lookup table based on tooth type and/or numbering). The desired orientation for a particular tooth can be determined by identifying with which tooth in the model the particular tooth corresponds. For example, the applicator device 100 can determine based on a tooth's shape or location in the mouth that the tooth is the number 8 right central incisor. The applicator can then determine the desired orientation for the number 8 right central incisor from a tooth model.

An amount of DCA and location on the tooth on which to apply the DCA is determined to give the tooth an appearance of having the desired orientation (506). For example, the applicator 100 can determine appropriate shading effects to apply to the tooth to so as to give the tooth the appearance of the desired orientation. The DCA is applied to the location of the tooth (508). For example, as described above, the processor 114 of the applicator device 100 can control the depositions system 112 to apply the appropriate amount of DCA to various locations of the tooth to create the desired effect.

Figure 6:
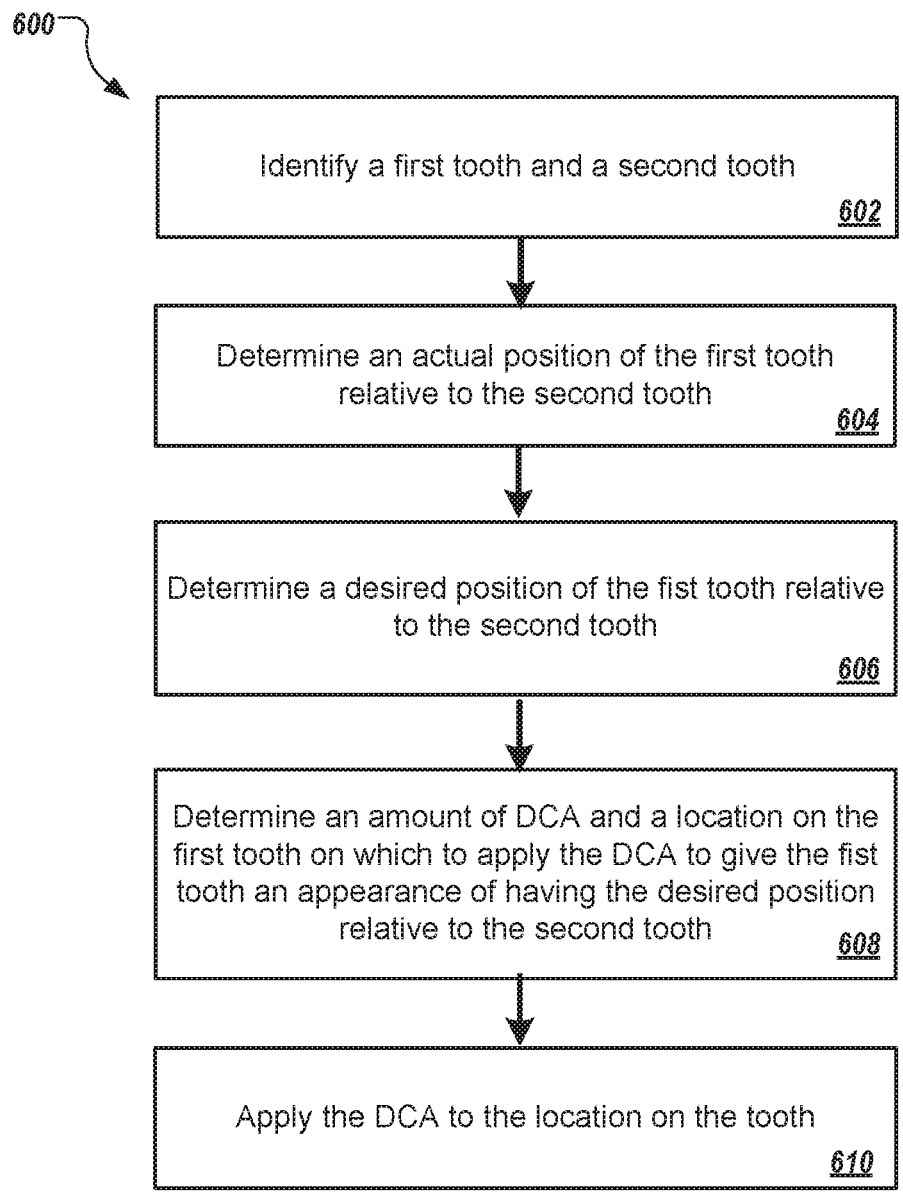
FIG. 6 depicts an example process for selectively applying a DCA to a tooth to adjust the apparent position of a tooth.

FIG. 6 depicts an example process 600 for selectively applying a DCA to a tooth to adjust the apparent position of a tooth that can be executed in accordance with implementations of the present disclosure. In some examples, the example process 600 can be provided as one or more computer-executable programs executed using one or more computing devices. In some examples, the process 600 is executed by an applicator device (e.g., applicator device 100 of FIGS. 1-3).

A first tooth and a second tooth are identified (602). As described above for example, image analysis techniques can be applied to an image of an area of the mouth to identify a tooth within the image. The processes described above can be used to identify a first and a second tooth. For example, the first and second tooth can generally be neighboring teeth. An actual position of the first tooth relative to the second tooth is determined (604). For example, the first tooth may be offset slightly behind the second tooth or slightly in front of the second tooth. The position can be determined, for example, based on shadowing on either or both of the first and second tooth. In some examples, as discussed above, a three-dimensional model of the area of the mouth can be generated from images of the area of the mouth. The position of first tooth relative to the second tooth can be determined from the three-dimensional model.

A desired position of the first tooth relative to the second tooth is determined (606). For example, the desired position of the first tooth can be chosen to correspond to respective position of the second, neighboring tooth such that the tooth does not appear to be offset either in front of or behind the second tooth. In some examples, the desired position of the tooth can be determined based on a standard model of human teeth (e.g., a lookup table based on tooth type and/or numbering). The desired position for a particular tooth relative to another tooth can be determined by identifying with which tooth in the model the particular tooth corresponds. For example, the applicator device 100 can determine based on a tooth's shape or location in the mouth that the tooth is the first tooth is the number 8 right central incisor and the second tooth is the number 7 right lateral incisor. The applicator can then determine the position for the number 8 right central incisor relative to the number 7 right lateral incisor from a tooth model.

An amount of DCA and location on the tooth on which to apply the DCA is determined to give the tooth an appearance of having the desired position (608). For example, the applicator 100 can determine appropriate shading effects to apply to the tooth to so as to give the tooth the appearance of the desired orientation. The DCA is applied to the location of the tooth (610). For example, as described above, the processor 114 of the applicator device 100 can control the depositions system 112 to apply the appropriate amount of DCA to various locations of the tooth to create the desired effect.

In some implementations, the DCAs may be cosmetic formulations that are designed to be applied in layers, with each layer having the effect of increasing opacity on the teeth and/or soft tissue of the mouth. For example, cosmetic formulations with very low pigment loads may be used to achieve a smoothing effect on the teeth and/or soft tissue of the mouth, for example, in the example ranges described in further detail below. The use of a cosmetic formulation with a color that is highly differentiated from the color of the area of the mouth to be treated may also be advantageous.

Implementations of the DCA are designed to be used with an applicator that, after each application, measures and compares the reflectance and/or color of the area on which the DCA is applied to those of the surrounding area to determine if the correction threshold has been achieved. For purposes of the present discussion, a DCA drop is the DCA from when it exits the deposition nozzle and is in flight until it contacts the target substrate. The DCA spot is the DCA on the target substrate, such as teeth and/or soft tissue of the mouth.

The DCA may have a low opacity, so that using an iterative application and feedback method, the optimal level of correction can be achieved without over correcting. Using a higher opacity DCA will allow more differentiated teeth and/or soft tissue features to be corrected with fewer applications, which may shorten the time for treatment. A disadvantage of a higher opacity DCA is that the DCA may look heavy on the corrected features and leave less differentiated features untouched, so that the treatment is incomplete. Conversely, using a DCA with very low opacity will allow more precise correction of features, but will require more applications and time.

The DCA may have a composition that causes it to rapidly adhere to the surface and cure, meaning dry and bind particles, such that successive applications in the same location build in layers without causing previous layers to dissolve. Moreover, the DCA may have a composition such that, when it is wet on the teeth and/or soft tissue of the mouth, it does not move and, as the volatile carrier evaporates the particulates, such as pigments, form a very thin layer. In some examples, an applicator device can include and evaporation mechanism to aid in carrier evaporation of a DCA (e.g., an infrared or UV light source). Ideally, the distribution of the mass of the particulates is Gaussian. An irregular distribution of mass within a circular area of consistent size may also yield acceptable visual results. A distribution of mass concentrated to the parameter of the circle and less in the middle, like a donut or volcano, will not yield visually acceptable results, because the edges will be visually sharp with higher contrast to the surroundings. In iterative, multi-layer approaches, such as those described herein, the irregular distribution of the pigment mass within each successive layer unevenly overlaps the first, creating a Gaussian distribution.

The DCA may have a composition that produces circular spots on a deposition surface that are approximately $\frac{1}{15}$" (1.7 mm) in diameter when used in one implementation of an applicator. Deposition spots of $\frac{1}{15}$" (1.7 mm) in diameter can be used to achieve visually appealing cosmetic treatments within a reasonable amount of time. Deposition spots smaller than $\frac{1}{15}$" (1.7 mm) in diameter can make an even more appealing result, because teeth and/or soft tissue features smaller than $\frac{1}{15}$" (1.7 mm) in diameter in the middle spatial frequencies can be corrected. A disadvantage of spots smaller than $\frac{1}{15}$" (1.7 mm) in diameter is that the treatment time will be extended. Conversely, using deposition spots larger than 1.7 mm will correct features larger than $\frac{1}{15}$" (1.7 mm) in diameter more quickly but leave smaller features untreated, which may create a less appealing result.

The DCA may have a composition such that the reflectance is highly differentiated from teeth and/or soft tissue of the mouth. Three axes of variability for the DCA are drop landing accuracy, spot shape and consistency, and spot size and consistency. The higher the opacity of the DCA and the more highly differentiated the DCA is from desired tooth and/or soft tissue color, the more accurate and consistent the deposition of DCA should be. Using a DCA that is the same as, or near to, the desired reflectance of the tooth and/or soft tissue and that has high opacity in a less accurate applicator may still yield acceptable visual results on very strong features.

The DCA may have a composition that works in the applicator to produce drops of consistent size, shape, viscosity and other physical properties for reliable operation of the applicator. In some implementations, a highly differentiated light cosmetic may be used to correct a dark tooth or soft tissue feature and may have particular ranges of characteristics. Example opacity ranges include 1%-40%, 2%-20% and 5%-15%. Example ranges of pigment particle size include 1-30 microns, 1-10 microns and 3-5 microns. The DCA can include a volatile carrier made of a mix of alcohols, water and other ingredients. Example ranges of alcohols in the volatile carrier include 12.0%-68.5% alcohols, 62.0%-68.5% alcohols and 66.6%-67.8% alcohols (e.g., % by weight). An example range for viscosity of the DCA includes 42-44 centipoise (cps).

Implementations of the present disclosure can be used for smoothing the appearance of the teeth and/or soft tissue, teeth whitening, simulated orthodontics (e.g., adjusting the apparent orientation and position of teeth), and applying visual effects. The application of DCAs with an apparatus of the present disclosure may also improve the appearance of stains, deposits, cracks, disease, and other imperfections as the device is moved over the area of the mouth. It is not typically necessary for a user to have a high skill level in order to use the deposition device (e.g., the applicator device 100 of FIGS. 1-3).

As discussed above, implementations of the present disclosure include a computerized handheld applicator that can be moved by a user in random directions. In some implementations, the arrangement of the deposition nozzles in a non-linear pattern enables rapid and precise application of one or more DCAs even in view of randomness of direction. In some implementations, three nozzles may be arranged in a triangle within a generally circular pattern. As a result, the user may achieve effective depositions by moving the applicator in random patterns, such as back and forth toothbrush-like movements, circles, straight lines, zigzags, and wavy lines. This freedom of movement is particularly useful for the iterative application of relatively small amounts of DCA to an area. Such application can be controlled by continual sensing of the area and software calculations of the amount of DCA to be deposited to that area after each sensing to create desired effects. Further, implementations of the present disclosure may use deposition nozzles, where each nozzle fires, or otherwise applies a DCA independently when a detected target, or nominated point on the teeth and/or soft tissue is beneath the particular nozzle.

As also discussed above, implementations of the present disclosure may use software methods on the computerized applicator that enable rapid and precise processing to create desired effects. In some implementations, this can be achieved through the random and typically iterative movement of the applicator over the area of the mouth. Examples of these software methods may include the use of a method for the prevention of undesirable deposition on the edges of defects. Further, implementations of the present disclosure provide for a rapid median average for calculating a target, or aim reflectance. The rapid median average can be performed only over the pixels surrounding a specific point to be treated, and only for the single pixel centered over the area immediately below a deposition nozzle, for example.

As also discussed above, implementations of the present disclosure provide for the use of DCA formulations that are designed to be applied iteratively in layers, with each layer having the effect of increasing opacity on the teeth and/or soft tissue of the mouth. For example, cosmetic formulations of DCA with very low pigment loads may be used to achieve a smoothing effect on the teeth and/or soft tissue. The low pigment load further enables the computerized applicator to create opacity in the deposition, so that repeated applications of relatively small amounts of DCA onto the same area can be used to create subtle desired effects. The application of DCA formulations in layers and with low pigment loads also enables the use of DCAs that are highly differentiated in luminance relative to the luminance of the area of the mouth to be treated.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method executed by one or more processors for selectively applying a dental care agent (DCA) to an area of a mouth, the method comprising:
   receiving, by the one or more processors, an image of the area of the mouth;
   identifying, within the image, a feature of interest;
   determining, by the one or more processors, an actual reflectance and an actual topology of the feature of interest;
   determining, by the one or more processors, a desired reflectance and a desired topology of the feature of interest;
   calculating, by the one or more processors, an amount of DCA to be applied to a portion of the feature of interest based on comparing the actual reflectance to the desired reflectance and the actual topology to the desired topology; and
   causing, by the one or more processors, the calculated amount of DCA to be applied to the portion of the feature of interest.

2. The method of claim 1, wherein determining the desired reflectance and the desired topology of the feature of interest comprises removing areas of high spatial frequency from the actual reflectance and actual topology of the feature of interest.

3. The method of claim 1, wherein the feature of interest is a tooth, and wherein the method further comprises:
   determining an actual orientation of the tooth;
   determining a desired orientation of the tooth;
   determining a second amount of DCA and a second portion of the tooth on which to apply the second amount of DCA to give the tooth an appearance of having the desired orientation; and
   causing the second amount of DCA to be applied to the second portion of the tooth.

4. The method of claim 1, wherein the feature of interest is a first tooth, and wherein the method further comprises:
   identifying, within the image, a second tooth;
   determining an actual position of the first tooth relative to the second tooth;
   determining a desired position of the first tooth relative to the second tooth;
   determining a second amount of DCA and a second portion of the first tooth on which to apply the second amount of DCA to give the first tooth an appearance of having the desired position relative to the second tooth; and
   causing the second amount of DCA to be applied to the second portion of the first tooth.

5. The method of claim 1, wherein the feature of interest is a tooth, and wherein the method further comprises:
   identifying, within the image, an interface between the tooth and a soft tissue; and
   causing a barrier DCA to be applied to the interface between the tooth and the soft tissue.

6. A handheld device for selectively applying a dental care agent (DCA) to an area of a mouth, the device comprising:
   at least one image generator; and
   one or more processors that are in communication with the at least one image generator and that are operable to perform operations comprising:
   receiving an image of a mouth;
   identifying, within the image, a feature of interest;
   determining an actual reflectance and an actual topology of the feature of interest;
   determining a desired reflectance and a desired topology of the feature of interest;
   calculating an amount of DCA to be applied to a portion of the feature of interest based on comparing the actual reflectance to the desired reflectance and the actual topology to the desired topology; and
   causing the calculated amount of DCA to be applied to the portion of the feature of interest.

7. The device of claim 6, wherein determining the desired reflectance and the desired topology of the feature of interest comprises removing areas of high spatial frequency from the actual reflectance and actual topology of the feature of interest.

8. The device of claim 6, wherein the feature of interest is a tooth, and wherein the operations further comprise:
   determining an actual orientation of the tooth;
   determining a desired orientation of the tooth;
   determining a second amount of DCA and a second portion of the tooth on which to apply the second amount of DCA to give the tooth an appearance of having the desired orientation; and
   causing the second amount of DCA to be applied to the second portion of the tooth.

9. The device of claim 6, wherein the feature of interest is a first tooth, and wherein the operations further comprise:
   identifying, within the image, a second tooth;
   determining an actual position of the first tooth relative to the second tooth;
   determining a desired position of the first tooth relative to the second tooth;
   determining a second amount of DCA and a second portion of the first tooth on which to apply the second amount of DCA to give the first tooth an appearance of having the desired position relative to the second tooth; and
   causing the second amount of DCA to be applied to the second portion of the first tooth.

10. The device of claim 6, wherein the feature of interest is a tooth, and wherein the operations further comprise:
    identifying, within the image, an interface between the tooth and a soft tissue; and
    causing a barrier DCA to be applied to the interface between the tooth and the soft tissue.

11. The device of claim 10, wherein the interface between the tooth and a soft tissue is identified based on colors within the image.

12. The device of claim 6, wherein the operations further comprise:
    identifying, within the image, a soft tissue;
    determining a reflectance of the soft tissue;
    determining a desired reflectance of the soft tissue;
    calculating an amount of DCA to be applied to a portion of the soft tissue based on comparing the actual reflectance of the soft tissue and the desired reflectance of the soft tissue; and
    causing the amount of DCA to be applied to the portion of the soft tissue.

13. The device of claim 6, wherein the operations further comprise determining an average direction of light that impinges a surface of the feature of interest, and wherein the desired reflectance and desired topology of the feature of interest are determined based on the average direction of light.

14. The device of claim 6, wherein the operations further comprise sending the image to a dental monitoring system.

15. The device of claim 6, wherein the operations further comprise:
   identifying a dental condition of the feature of interest; and
   sending an indication of the dental condition to a dental monitoring system.

16. A non-transitory computer-readable storage medium coupled to one or more processors and having instructions stored thereon which, when executed by the one or more processors, cause the one or more processors to perform operations for selectively applying a dental care agent (DCA) to an area of a mouth, the operations comprising:
   receiving an image of a mouth;
   identifying, within the image, a feature of interest;
   determining an actual reflectance and an actual topology of the feature of interest;
   determining a desired reflectance and a desired topology of the feature of interest;
   calculating an amount of DCA to be applied to a portion of the feature of interest based on comparing the actual reflectance to the desired reflectance and the actual topology to the desired topology; and
   causing the calculated amount of DCA to be applied to the portion of the feature of interest.

17. The medium of claim 16, wherein determining the desired reflectance and the desired topology of the feature of interest comprises removing areas of high spatial frequency from the actual reflectance and actual topology of the feature of interest.

18. The medium of claim 16, wherein the feature of interest is a tooth, and wherein the operations further comprise:
   determining an actual orientation of the tooth;
   determining a desired orientation of the tooth;
   determining a second amount of DCA and a second portion of the tooth on which to apply the second amount of DCA to give the tooth an appearance of having the desired orientation; and
   causing the second amount of DCA to be applied to the second portion of the tooth.

19. The medium of claim 16, wherein the feature of interest is a first tooth, and wherein the operations further comprise:
   identifying, within the image, a second tooth;
   determining an actual position of the first tooth relative to the second tooth;
   determining a desired position of the first tooth relative to the second tooth;
   determining a second amount of DCA and a second portion of the first tooth on which to apply the second amount of DCA to give the first tooth an appearance of having the desired position relative to the second tooth; and
   causing the second amount of DCA to be applied to the second portion of the first tooth.

20. The medium of claim 16, wherein the feature of interest is a tooth, and wherein the operations further comprise:
   identifying, within the image, an interface between the tooth and a soft tissue; and
   causing a barrier DCA to be applied to the interface between the tooth and the soft tissue.

* * * * *